United States Patent [19]

Nadler et al.

[11] Patent Number: 5,712,284
[45] Date of Patent: Jan. 27, 1998

[54] AZALICYCLOOCTANE DERIVATIVES AS ANTI-ARRHYTHMIC AGENTS

[75] Inventors: Guy Marguerite Marie Gerard Nadler; Michel Louis Souchet, both of Rennes, France

[73] Assignee: SmithKline Beecham Laboratoires Pharmaceutiques, Nanterre Cedex, France

[21] Appl. No.: 578,667

[22] PCT Filed: Jul. 11, 1994

[86] PCT No.: PCT/EP94/02299

§ 371 Date: Feb. 14, 1996

§ 102(e) Date: Feb. 14, 1996

[87] PCT Pub. No.: WO95/03301

PCT Pub. Date: Feb. 2, 1995

[30] Foreign Application Priority Data

Jul. 22, 1993 [FR] France .................... 93 09017

[51] Int. Cl.$^6$ ................ A61K 31/435; C07D 451/04
[52] U.S. Cl. ................ 514/299; 514/304; 546/112; 546/124
[58] Field of Search ................ 546/112, 124; 514/304, 299

[56] References Cited

U.S. PATENT DOCUMENTS

| | | | |
|---|---|---|---|
| 5,070,094 | 12/1991 | Fowler | 514/304 |
| 5,084,572 | 1/1992 | Berlin | 546/18 |

FOREIGN PATENT DOCUMENTS 0 416 521 A1    3/1991    European Pat. Off. .

*Primary Examiner*—C. Warren Ivy
*Assistant Examiner*—Evelyn Huang
*Attorney, Agent, or Firm*—Mary E. McCarthy; Stephen Venetianer; Edward T. Lentz

[57] ABSTRACT

A compound of formula (I) or a salt thereof, or a solvate thereof:

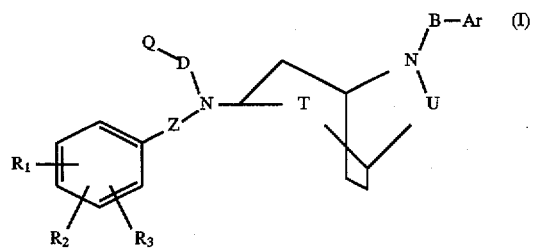

wherein B represents a $C_{1-4}$ n-alkylene group wherein each carbon is optionally substituted by a $C_{1-6}$ alkyl group; Z represents a bond, $CH_2$, $(CH_2)_2$ or $X$—$CH_2$—$CH_2$ wherein X represents O or S; D represents CO, $SO_2$, NH—CO or NH—$SO_2$; T represents a bond and U represents $CH_2$ or T represents $CH_2$ and U represents a bond; Q represents aryl, aralkyl, aralkenyl or aralkynyl, wherein the aryl moiety may be unsubstituted or substituted with 1 to 5 substituents selected from the list consisting of nitro, halogen, alkylsulfonamido, acylamido, 1H-imidazolyl, alkyl or haloalkyl, or Q represents substituted or unsubstituted: furanyl, pyranyl, thienyl, thiazolyl, imidazolyl, triazolyl or the benzo fused equivalents or furanyl, pyranyl, thienyl, thiazolyl, 1H-imidazolyl, or triazolyl, indolyl, oxoindolyl, indenyl, isoindenyl, indazolyl, indolizinyl or pyridinyl or cycloalkyl optionally fused to an aryl group; $R_1$, $R_2$, and $R_3$ each independently represents H, alkyl, OH or alkoxy or, if attached to adjacent carbon atoms, any two of $R_1$, $R_2$, and $R_3$ together with the carbon atoms to which they are attached may form a fused heterocyclic ring of five or six atoms wherein one, two or three of the said atoms are oxygen or nitrogen; Ar represents substituted or unsubstituted aryl, wherein the optional substituents are the above defined $R_1$, $R_2$, and $R_3$ or Ar represents a substituted or unsubstituted heteroaryl group; a process for the preparation of such a compound and the use of such a compound in medicine.

10 Claims, No Drawings

AZALICYCLOOCTANE DERIVATIVES AS ANTI-ARRHYTHMIC AGENTS

This application is the national phase of PCT/EP 94/02299, filed on Jul. 11, 1994.

The invention relates to certain novel compounds, to pharmaceutical compositions containing such compounds, to a process for the preparation of such compounds and to the use of such compounds as active therapeutic agents, particularly in the treatment of atrial or ventricular cardiac arrhythmias.

European Patent Application Number 0416521 discloses certain N-benzyltropaneamides which are stated to have activity as Class III antiarrhythmic agents, acting by prolonging cardiac action potential duration.

Chemical Abstracts 117:778 discloses 4-chloro-N-(4-methoxyphenyl-N-[9-(2-phenylethyl)-9-azabicyclo [3.3.1] non-3-yl and related anaesthetic compounds.

The Journal of Heterocyclic Chemistry (1978), 15, 273–280 discloses N-substituted 5- and 6-propanilido-2-Azabicyclo[2.2.2]octanes which are stated to analgesics.

The Journal of Heterocyclic Chemistry 31, 313–318, 1994 discloses a series of N-phenylethyl-8-β-amidocamphidines and the use of such compounds to study the influence of certain stereochemical factors on analgesia in this class of compounds.

The Journal of Medicinal Chemistry 1993, Vol. 36, No. 23, 3707–3720, discloses certain 9-azabicyclo [3.3.1]nonan-3β-yl benzamides and their affinity for dopamine $D_2$, dopamine $D_3$, serotonin 5-$HT_3$ and $\alpha_2$ adrenergic receptors.

Anti-arrhythmic agents are classified according to their electrophysiological effects on the cardiac cell (Vaugham-Williams, 1970, 1989): class I agents block the fast sodium cent, class II agents are beta-adrenergic blockers, class III agents block potassium currents, class IV agents block the calcium current, and class V agents are specific sinus node inhibitors.

A majority of ventricular and atrial arrhythmias are related to reentrant circuit. The prolongation of myocardial refractoriness within or surrounding such a reentrant circuit is a potential mechanism for the management of cardiac arrhythmias.

Because class III antiarrhythmic agents block cardiac potassium currents, they prolong the repolarisation process and increase refractoriness. Consequently class III agents represent the most specific class to treat reentrant arrhythmias.

However, due to their mechanism of action, i.e. a concentration dependent increase in the cardiac action potential duration, higher doses of class III antiarrhythmic agents may trigger arrhythmias. Such arrhythmias, called Torsade de Pointe represent the main adverse effect for all pure class III compounds currently in development.

It has been discovered that certain novel substituted azabicyclooctane derivatives induce a self-limiting increase of the cardiac action potential duration, related to a dual blockade of cardiac potassium and calcium channels. Consequently, they have an improved pharmacological profile over pure class III anti-arrhythmic agents, in particular they are indicated to have a low proarrhythmic potential and to restore the contractile function of the ischaemic myocardium.

Accordingly, the present invention provides a compound of formula (I):

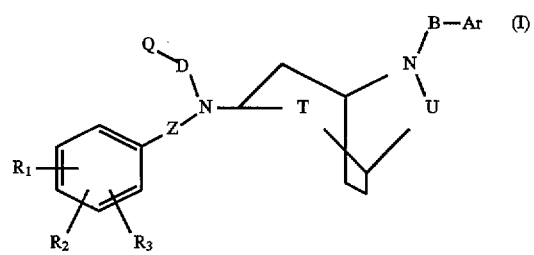

or a salt thereof, or a solvate thereof, wherein

B represents a $C_{1-4}$ n-alkylene group wherein each carbon is optionally substituted by a $C_{1-6}$ alkyl group;

Z represents a bond, $CH_2$, $(CH_2)_2$ or X—$CH_2$—$CH_2$ wherein X represents O or S;

T represents a bond and U represents $CH_2$ or T represents $CH_2$ and U represents a bond;

D represents CO, $SO_2$, NH—CO or NH—$SO_2$;

Q represents aryl, aralkyl, aralkenyl or aralkynyl, wherein the aryl moiety may be unsubstituted or substituted with 1 to 5 substituents selected from the list consisting of nitro, halogen, alkylsulfonamido, acylamido, 1H-imidazoyl, alkyl or haloalkyl, or Q represents substituted or unsubstituted: furanyl, pyranyl, thienyl, thiazolyl, imidazolyl, triazolyl or the benzo fused equivalents of furanyl, pyranyl, thienyl, thiazolyl, 1H-imidazolyl or triazolyl, indolyl, oxoindolyl, indenyl, isoindenyl, indazolyl, indolizinyl or pyridinyl or cycloalkyl optionally fused to an aryl group;

$R_1$, $R_2$ and $R_3$ each independently represents H, alkyl, OH or alkoxy or, if attached to adjacent carbon atoms, any two of $R_1$, $R_2$ or $R_3$ together with the carbon atoms to which they are attached may form a fused heterocyclic ring of five or six atoms wherein one, two or three of the said atoms are oxygen or nitrogen;

Ar represents substituted or unsubstituted aryl, wherein the optional substituents are the above defined $R_1$, $R_2$ and $R_3$ or Ar represents a substituted or unsubstituted heteroaryl group..

Suitably, B represents $CH_2CH_2$

Suitably, Z represents a bond.

Suitably, T represents a bond and U represents $CH_2$.

Suitably, T represents $CH_2$ and U represents a bond.

Suitably, D represents CO.

Suitably, Q is phenyl, favourably substituted phenyl.

An example of a substituent for Q is a nitro group.

Suitably, one or two of $R_1$, $R_2$ and $R_3$ represents alkoxy, for example methoxy, the remaining member(s) being H.

As used herein, the term "alkyl" includes straight or branched chain alkyl groups having from 1 to 12, favourably 1 to 6, carbon atoms and shall include such alkyl groups when forming part of other groups such as alkoxy or arylalkyl groups.

As used herein, the term "alkenyl" includes straight or branched chain alkylene groups having from 2 to 12, favourably 2 to 6, carbon atoms and one or more double bonds.

As used herein, the term "alkynyl" includes straight or branched chain alkylene groups having from 2 to 12, favourably 2 to 6, carbon atoms and one or more triple bonds.

As used herein the term "aryl" includes phenyl and naphthyl, preferably phenyl, optionally substituted with up to five, preferably up to three, groups selected from halogen, alkyl, phenyl, alkoxy, haloalkyl, hydroxyalkyl, hydroxy, amino, nitro, cyano, carboxy, alkoxycarbonyl, alkoxycarbonylalkyl, alkylcarbonyloxy or alkylcarbonyl groups.

Suitable heteroaryl groups include indole, benzofuran and benzothiophene groups, substituted as described herein with regard to the aryl group.

As used herein, the term "cycloalkyl" includes cyclic alkyl carbon-carbon linkages of four to seven carbon atoms.

As used herein "halogen" includes fluorine, chlorine or bromine.

As used herein, the term "alkylsulfonamido" includes a radical of the formula

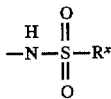

wherein $R^x$ is an alkyl group.

As used herein, the term "cardiac arrhythmia" relates to any variation from the normal rhythm of heart beat, including, without limitation, sinus arrhythmia, premature heartbeat, heartblock, fibrillation, flutter, tachycardia, paroxysmal tachycardia and premature ventricular contractions.

The compounds of formula (I) may possess chiral carbon atoms and therefore may exist in more than one stereoisomeric form. The invention extends to any of the stereoisomeric forms, including enantiomers of the compounds of formula (I) and to mixtures thereof, including racemates. The different stereoisomeric forms may be separated or resolved one from the other by conventional methods or any given isomer may be obtained by conventional stereospecific or asymmetric syntheses.

Suitable salts are pharmaceutically acceptable salts.

The pharmaceutically acceptable salts of the compounds of formula (I) include acid addition salts with pharmaceutically acceptable mineral acids such as hydrochloric, hydrobromic, boric, phosphoric, sulphuric and pharmaceutically acceptable organic acids such as acetic, tartaric, maleic, citric, succinic, benzoic, ascorbic, methanesulphonic, a-keto-glutaric, a-glycerophosphoric, and glucose-1-phosphoric acids. Preferably the acid addition salt is a hydrochloride.

Pharmaceutically acceptable salts also include quaternary salts. Examples of quaternary salts include such compounds quaternised by compounds such as $R^y$-T wherein $R^y$ is $C_{1-6}$ alkyl, phenyl-$C_{1-6}$ alkyl or $C_{5-7}$ cycloalkyl, and T is a moiety corresponding to an anion of an acid. Suitable examples of $R^y$ include methyl, ethyl and n- and iso- propyl; and benzyl and phenethyl. Suitably T includes halide such as chloride, bromide and iodide.

Pharmaceutically acceptable salts also include pharmaceutically acceptable N-oxides, and the invention extends to these.

The compounds of the formula (I) and their salts may also form solvates, especially pharmaceutically acceptable solvates, such as hydrates, and the invention extends to these, and especially to the pharmaceutically acceptable solvates.

The salts of the compounds of the formula (I) which are not pharmaceutically acceptable may be useful as intermediates in the preparation of pharmaceutically acceptable salts of compounds of formula (I) or the compounds of the formula (I) themselves, and as such form an aspect of the present invention.

A compound of formula (I) or a salt thereof, or a solvate thereof, may be prepared by reacting a compound of formula (II):

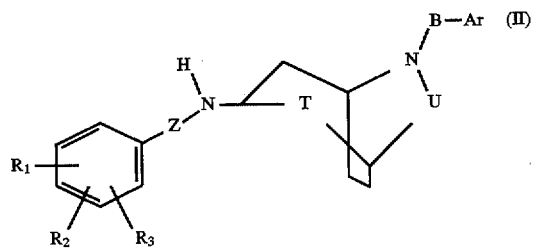

wherein B, Z, T, U, $R_1$, $R_2$, $R_3$ and Ar are as defined in relation to formula (I) with a reagent of formula (III);

wherein Q is as defined in relation to formula (I) and:

(a) for compounds of formula (I) wherein D is CO or $SO_2$, $L^1$ represents COX or $SO_2X$ respectively, wherein X is a leaving group such as a halogen; and (b) for compounds of formula (I) wherein D is NH—CO, $L^1$ is N=C=O;

(c) for compounds of formula (I) wherein D is NH—$SO_2$, $L^1$ is NH—$SO_2.N_3$;

and thereafter, if required preparing a pharmaceutically acceptable salt of the compound of formula (I) and/or a pharmaceutically acceptable solvate thereof.

The reaction conditions for the reaction between compounds of formulae (II) and (III) are conventional conditions appropriate to the nature of the reagent used, generally however the reaction may be carried out in an inert solvent, such as methylene chloride, at any suitable temperature providing a convenient rate of formation of the desired product, generally at an ambient to elevated temperature, conveniently at the reflux temperature of the solvent and preferably in the presence of a base such as triethylamine.

The compounds of formula (II) may be prepared by reducing a compound of formula (IV):

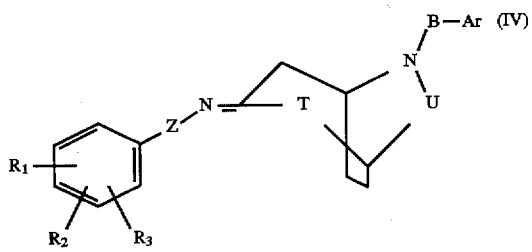

wherein B, Z, T, U, $R_1$, $R_2$, $R_3$ and Ar are as defined in relation to formula (I).

The reduction of the compound of formula (IV) may be effected using any appropriate reduction method, for example metal hydride reduction using a lithium hydride such as lithium aluminium hydride in an aprotic solvent such as tetrahydrofuran (THF), or with sodium cyanoborohydride in a protic solvent such as methanol in the presence of methanolic HCl, or with sodium in an alcohol such as pentanol, at any suitable temperature which provides a convenient rate of reaction, generally at ambient to an elevated temperature, conveniently at ambient temperature for the metal hydride reduction or at reflux for the sodium alcohol reduction.

A compound of formula (IV) may be prepared by reacting a compound of formula (V):

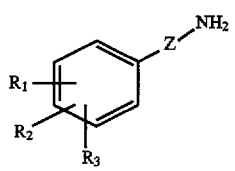

wherein Z, R₁, R₂ and R₃ are as defined in relation to formula (I), with a compound of formula (VI):

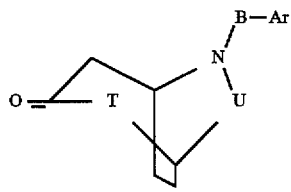

wherein B, T, U and Ar are as defined in relation to the compound of formula (I).

The reaction between the compounds of formulae (V) and (VI) may be carried out in a solvent such as toluene, with a suitable catalyst such as p-toluenesulfonic acid, at any suitable temperature providing a convenient rate of formation of the desired product, generally at an elevated temperature and conveniently at the reflux temperature of the solvent; or in methanol at ambient temperature; the water produced in the reaction may be removed by any conventional means, for example by means of a Dean and Stark apparatus.

The ketones of formula (VI) wherein T is $CH_2$ and U is a bond, are known compounds or they may be obtained by procedures analogous to those used to prepare known compounds, for example by means of a Robinson-Schöpf cyclisation following the general procedure described by P. Doster, T. Himbert, M. Langlois, B. Bucher and G. Mocquet in Eur. J. Meal. Chem. 1984, 19, 105–110 and summarized in Scheme 1:

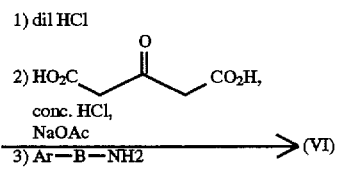

The ketones of formula (VI) wherein T is bond and U is $CH_2$, may be prepared by reacting a compound of formula (VII):

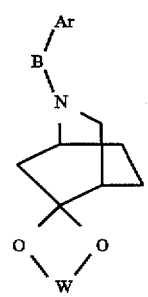

wherein B and Ar are as defined in relation to the compound of formula (I) and W is an alkylene chain, conveniently 2,2-dimethylpropyl, in acidic medium for example aqueous HCl, at any suitable temperature providing a convenient rate of formation of the desired product, generally at an ambient to elevated temperature, conveniently at 60° C.

A compound of formula (VII) may be obtained by procedures analogous to those used to prepare known compounds, for example those disclosed by S. J. Law et al. in J. Heterocyclic Chem. 1978, 15, 273 and summarized in Scheme 2.

Scheme 2 in which Ar, B and W are as defined above:

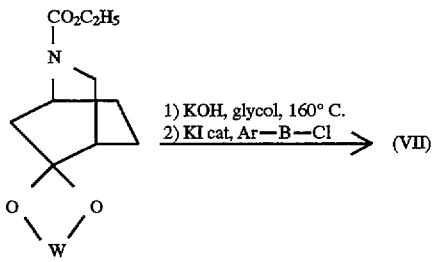

The compounds of formulae (III) are known commercially available compounds or they may be obtained by procedures analogous to those used to prepare known compounds, for example compounds of formula (III): wherein $L^1$ represents CO.X may be prepared according to methods described in *Organic Syntheses* Coll. Vol. I, page 394 or *Organic Syntheses* Coll. Vol. III, page 29, wherein $L^1$ represents $SO_2X$ according to methods described in *Organic Syntheses* Coll. Vol. VIII, page 104 and for compounds of formula (III) wherein $L^1$ represents N=C=O according to methods described in *Organic Syntheses* Coll. Vol. III, page 846. Also the compounds of formula (III) wherein $L^1$ represents $NH.SO_2.N_3$ may be prepared according to methods described in *J. Medical Chemistry*, (1972), 15, 538.

It will be appreciated that in any of the abovementioned reactions any reactive group in the substrate molecule may be protected, according to conventional chemical practice.

Suitable protecting groups in any of the abovementioned reactions are those used conventionally in the art. The methods of formation and removal of such protecting groups are those conventional methods appropriate to the molecule being protected.

As mentioned above the compounds of the invention are indicated as having useful therapeutic properties: The present invention accordingly provides a compound of formula (I), or a pharmaceutically acceptable salt thereof and/or a pharmaceutically acceptable solvate thereof, for use as an active therapeutic substance.

More particularly, the present invention provides a compound of formula (I), or a pharmaceutically acceptable salt thereof and/or a pharmaceutically acceptable solvate thereof, for use in the treatment of and/or prophylaxis of arrhythmia, especially cardiac arrhythmia such as ventricular arrhythmia, and also ischeamic rhythm disorders.

A compound of formula (I), or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a pharmaceutically acceptable salt thereof, or a pharmaceutically acceptable solvate thereof, and a pharmaceutically acceptable carrier thereof.

A compound of formula (I) or a pharmaceutically acceptable salt thereof and/or a pharmaceutically acceptable solvate thereof is normally administered in unit dosage form.

An amount effective to treat the disorder hereinbefore described depends upon such factors as the efficacy of a compound of formula (I), the particular nature of the pharmaceutically acceptable salt or pharmaceutically acceptable solvate chosen, the nature and severity of the disorders being treated and the weight of the mammal. However, a unit dose will normally contain 1 to 50 mg for example 2 to 15 mg, of the compound of the invention.

Unit doses will normally be administered once or more than once a day, for example 2, 3, 4, 5 or 6 times a day, more usually 2 to 4 times a day, such that the total daily dose is normally in the range, for a 70 kg adult of 1 to 300 mg, more usually 4 to 100 mg, for example 10 to 60 mg, that is in the range of approximately 0.02 to 5 mg/kg/day, more usually 0.1 to 2 mg/kg/day, for example 0.1 to 0.5 mg/kg/day.

In such treatment, the compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the compound and may be prepared in a conventional manner, for example, as described in the standard textbooks such as 'Dermatological Formulations'—B. W. Barry (Drugs and the Pharmaceutical Sciences—Dekker) or Harrys Cosmeticology (Leonard Hill Books).

In addition such compositions may contain further active agents such as anti-hypertensive agents and diuretics.

As is common practice, the compositions will usually be accompanied by written or printed directions for use in the medical treatment concerned.

As used herein the ten 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of arrhythmia, especially cardiac arrhythmia such as ventricular arrhythmia, and also ischeamic rhythm disorders in a human or non-human mammal which comprises administering an effective, non-toxic, amount of a compound of the general formula (I), or a pharmaceutically acceptable salt thereof and/or a pharmaceutically acceptable solvate thereof to a human or non-human mammal in need thereof.

Conveniently, the active ingredient may be administered as a pharmaceutical composition hereinbefore defined, and this forms a particular aspect of the present invention.

In the treatment and/or prophylaxis of arrhythmia and/or ischeamic arrhythmia disorders the compound of the general formula (I), or a pharmaceutically acceptable salt thereof and/or a pharmaceutically acceptable solvate thereof, may be taken in doses, such as those described above.

Similar dosage regimens are suitable for the treatment and/or prophylaxis of non-human mammals.

In a further aspect the present invention provides the use of a compound of formula (I), or a pharmaceutically acceptable salt thereof and/or a pharmaceutically acceptable solvate thereof, for the manufacture of a medicament for the treatment of arrhythmia, especially cardiac arrhythmia such as ventricular arrhythmia, and also ischeamic rhythm disorders.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the active compound and may be prepared in a conventional manner, for example, as described in the standard textbooks such as 'Dermatological Formulations'—B. W. Barry (Drugs and the Pharmaceutical Sciences—Dekker) or Harrys Cosmeticology (Leonard Hill Books).

No toxicological effects are indicated when an active compound is administered in the above mentioned dosage ranges.

The following Examples illustrate the invention but do not limit it in any way.

Description 1
8-[2-(3,4-Dimethoxyphenyl)ethyl]-8-aza-bicyclo[3.2.1] octan-3-one.

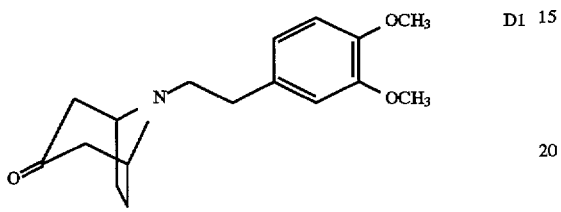
D1

Following a general procedure previously described (P. Doster et al. Eur. I. Med. Chem. 1984, 19, 105), 8.2 g (62 mmol) 2,5-dimethoxytetrahydrofuran were heated at 80° C. in 75 ml of 0.1N aqueous HCl for 1 h. After cooling to 10° C., 10 g (68.4 mmol) acetone dicarboxylic acid, 12.4 g (68.5 mmol) 2-(3,4-dimethoxyphenyl)ethylamine, 6.13 g (74.7 mmol) sodium acetate and 5.7 ml 12N aqueous HCl were added wile stirring. Stirring was maintained overnight at room temperature. The aqueous mixture was neutralized and extracted with methylene chloride. The organic phase was washed with brine, dried over $MgSO_4$ and concentrated. The filtrate was concentrated and the residual oil was purified by chromatography on silica gel using ethyl acetate as eluent, affording 12 g of an oil pure by TLC.

$^1$H NMR($CDCl_3$) δ(ppm): 1.51–1.68 (m,2H); 1.95–2.11 (m,2H); 2.20 (broad d,J=15.2Hz,2H); 2.67 (dd,J=4.3Hz and 16.0Hz,2H); 2.82 (broad band,4H); 3.52–3.64 (m,2H); 3.86 (s,3H,$OCH_3$); 3.88 (s,3H, $OCH_3$); 6.71–6.86 (m,3H).

Description 2
N-(3,4-Dimethoxyphenyl)-8-[2-(3,4-dimethoxyphenyl) ethyl]-8-aza-bicyclo[3.2.1]octan-3-amine.

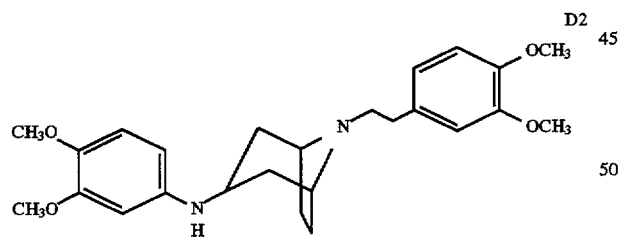
D2

To a stirred solution of 4 g (26 mmol) 3,4-dimethoxyaniline and 5 ml 14N methanolic HCl in 200 ml methanol, were added 5.7 g (20 mmol) of 8-[2-(3,4-dimethoxyphenyl)ethyl]-8-azabicyclo[3.2.1]octane-3-one (D1), followed by addition of 1 g (16 mmol) sodium cyanoborohydride. The reaction mixture was stirred overnight, slightly acidified and concentrated to dryness. The crude residue was filtered over a short column of silica gel using 95:5 methylene chloride:methanol. The expected fraction was triturated with ethyl acetate affording 4 g (47%) of the desired compound. mp.: 220° C. $^1$H NMR shows a mixture of two conformations of the title compound.

$^1$H NMR($CDCl_3$) δ(ppm): 1.85–2.01 (broad d,J=14.7Hz, 2H); 2.03–2.45 (m,4H); 2.71–3.25 (broad m,6H); 3.70–3.90 (m, 1H) overlapped by 3.61–3.76 (m,2H), 3.81 (s,3H, $OCH_3$), 3.83 (s,3H, $OCH_3$), 3.85 (s,3H,$OCH_3$); 6.10 (dd,J=2.4Hz, J'8=2Hz, 1H); 6.21 (dd,J= 2.4Hz, 1H); 6.75 (d,J'=8.2Hz, 1H); 6.79 (2H); 6.86 (1H).

Description 3
2-[2-(3,4-Dimethoxyphenyl)ethyl]-spiro[5',5'-dimethyl-2-azabicyclo[2.2.2]octane-5,2'-[1',3']-dioxane]

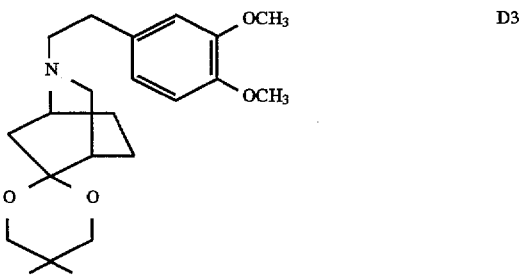
D3

Following a general procedure previously described (S-J. Law et al., J. Heterocyclic Chem., 1978, 15, 273), a mixture of 11.9 g (42 mmol) of spiro[ethyl 5',5'dimethyl-2-azabicyclo[2.2.2]octane-5,2'-[1',3']-dioxane-2-carboxylate] and 11.8 g (210 mmol) of potassium hydroxide in 120 ml of ethylene glycol was heated at 160° C. under argon for 14 hours. The reaction mixture was cooled, diluted with 150 ml of water, and extracted with methylene chloride (3×100 ml). The combined extracts were washed with water (2×50 ml), dried over $MgSO_4$ and evaporated to give a viscous brown oil which was dissolved in 80 ml of acetonitrile. 6.8 g (34 mmol) of 2-(3,4-dimethoxyphenyl)-1-chloroethane, 3.22 g (32 mmol) of triethylamine, and a catalytic amount of KI were added. The reaction mixture was refluxed for 30 h then stirred at room temperature for 48 h. The reaction mixture was concentrated in vacuo, diluted with methylene chloride, washed with water, dried over $MgSO_4$, and concentrated in vacuo. 8.8 g of a white solid pure by TLC was isolated.

$^1$H NMR ($CDCl_3$)δ(ppm): 0.93(s,3H); 1.01(s,3H); 1.58–1.80(m,2H); 1.80–2.05(m,3H); 2.15–2.75(m,3H); 2.90–3.30(m,5H); 3.40–3.60(m,5H); 3.85(s,3H); 3.88(s, 3H); 6.75–6.85(m,3H).

Description 4
2-[2-(3,4-Dimethoxyphenyl)ethyl]-2-azabicyclo[2.2.2] octan-5-one

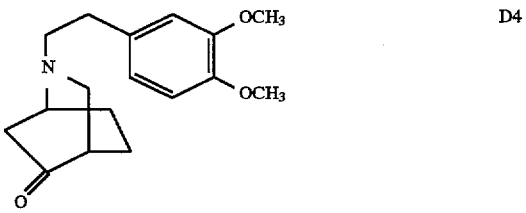
D4

A mixture containing 380 mg (mmol) of 2-[2-(3,4-dimethoxyphenyl)ethyl]-spiro[5',5'-dimethyl-2-azabicyclo [2.2.2octane-5,2'-[1',3']-dioxane] (D3) and 6 ml of 10% aqueous HCl was heated at 60° C. for 18 h. The reaction mixture was washed with methylene chloride (3×5ml). The aqueous solution was treated with sodium carbonate and extracted with methylene chloride (3×10ml). The combined organic extracts were dried over $MgSO_4$, and concentrated in vacuo leading to 250 mg of a clean product by TLC.

$^1$H NMR ($CDCl_3$)δ(ppm): 1.55–1.70(m,1H); 1.75–2.10 (m,2H); 2.15–2.30(m,2H); 2.30–2.40(m, 1H); 2.60–2.85(m, 5H); 2.85–3.05(m, 1H); 3.05–3.20(m,2H); 3.85(s,3H); 3.87 (s,3H); 6.65–6.85(m,3H).

Description 5
N-(3,4-Dimethoxyphenyl)-2-[2-(3,4-dimethoxy-phenyl) ethyl]-2-azabicyclo[2.2.2]octan-5-amine

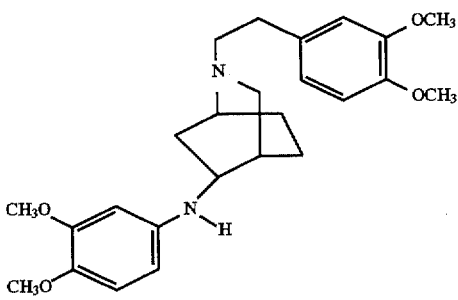

1.58 g (5.5 mmol) of 2-[2-(3,4-dimethoxyphenyl)ethyl]-2-azabicyclo[2.2.2]octan-5-one (D4) was added to a solution of 1.10 g (7.2 mmol) of 3,4-dimethoxyaniline in 30 ml of MeOH and 1.4 ml of methanolic HCl. 274 mg (4.3 mmol) of sodium cyanoborohydride was then added. The reaction mixture was allowed to stir at room temperature overnight. Concentrated aqueous HCl (1.8 ml) was added and the mixture was concentrated in vacuo. The residue was token up with 50 ml of water and 3 ml of 15% aqueous NaOH and extracted with methylene chloride (3×30 ml). The combined organic extracts were dried over MgSO$_4$ and concentrated in vacuo, giving rise to 1.38 g of a clean product (mixture of stereoisomers) after purification by filtration through a pad of silica gel. The stereoisomers were separated by flash chromatography on silica gel using methanol: methylene chloride (5:95) as eluent.

$^1$H NMR (CDCl$_3$)δ(ppm) isomer I: 1.50–2.00 (m,3H); 2.00–2.45(m, 4H); 2.50–2.80(m, 1H); 3.00–3.25(m,4H); 3.25–3.35(m, 1H); 3.60–3.75(m,2H); 3.79(s,3H); 3.84(s, 3H); 3.85(s,3H); 3.88(s,3H); 6.11 (dd,J$_1$=2.5Hz,J$_2$=8.5Hz, 1H); 6.38(d,J=2.5Hz,1H); 6.71(d,J=8.5Hz, 1H); 6.75–6.85 (m,3H).

Isomer II: 1.30–1.50(m,2H); 1.55–1.80(m,3H); 1.85–2.25 (m,3H); 2.75–3.60(m,7H); 3.80(s,3H); 3.84(s,3H); 3.85(s, 3H); 3.88(s,3H); 6.13(dd,J$_1$=2.5Hz,J$_2$=8.5Hz, 1H); 6.27(d, J=2.5Hz, 1H); 6.72(d,J=8.5Hz, 1H); 6.75–6.90(m,3H).

EXAMPLE 1

N-(3,4-Dimethoxyphenyl)-N-[8-[2-(3,4-dimethoxyphenyl)ethyl]-8-aza-bicyclo[3.2.1]oct-3-yl]-4-nitrobenzamide, hydrochloride.

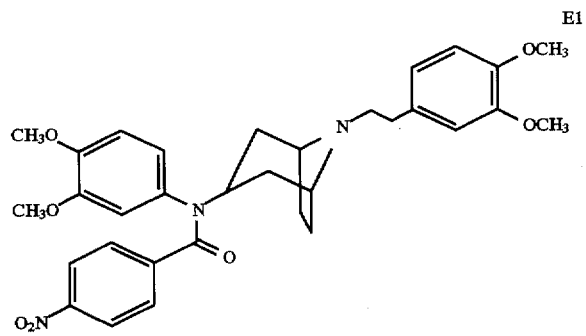

To a room temperature stirred solution of 1 g (2.3 mmol) of N-(3,4-dimethoxyphenyl)-8-[2-(3,4-dimethoxyphenyl) ethyl]-8-aza-bicyclo[3.2.1]octan-3-amine (D2) and 0.3 g (2.8 mmol) of triethylamine in 50 ml of chloroform, were added dropwise 0.5 g (2.7 mmol) of 4-nitrobenzoyl chloride. Stirring was then continued at more temperature for 4 hours. The mixture was washed successively with water, diluted aqueous HCl, water, diluted aqueous NaOH, water, then dried over MgSO$_4$ and concentrated. The residue was purified by chromatography on silica gel using 95:5 methylene chloride:methanol. The desired fraction was recrystallised from ethyl acetate affording the free base of the title compound as white crystals of mp.:163° C.

$^1$H NMR(CDCl$_3$)δ(ppm): 1.26–1.60 (m,4H); 1.86–2.10 (m,2H); 2.30–2.64 (m,4H); 2.64–2.82 (m,2H); 3.23–3.50 (m,2H); 3.75 (s,3H,OCH$_3$); 3.81 (s,3H,OCH$_3$); 3.85 (s,3H, OCH$_3$); 3.88 (s,3H,OCH$_3$); 4.73–5.08 (m,1H); 6.34–6.94 (m,6H); 7.37 (broad d,J=8.23Hz,2H); 7.99 (broad d,J= 8.23Hz,2H).

The product was then dissolved in a 1:1 mixture of methylene chloride:ethyl acetate and 0.7 ml of 0.55M anhydrous HCl in ether were added. The mixture was partly concentrated, then it crystallised affording 230 mg of the title compound as pale yellow crystals. mp.:165°–167° C.

$^1$H NMR(CDCl$_3$)δ(ppm): 2.13–2.61 (m,6H); 2.91–3.18 (m,4H); 3.18–3.34 (m,2H); 3.65–4.00 (m,2H) overlapped by 3.79 (s,3H,OCH$_3$), 3.83 (s,3H,OCH$_3$), 3.86 (s,3H,OCH$_3$), and 3.88 (s,3H,OCH$_3$); 4.91–5.20 (m,1H); 6.41 (dd,1H); 6.52–6.66 (m,2H); 6.80 (broad band,2H); 6.88 (broad s, 1H); 7.43 (broad d,J=8.91Hz,2H); 8.03 (broad d,J=8.91Hz, 2H); 11.97 (broad band,1H exchangeable with D$_2$O).

Example 2

N-(3,4-Dimethoxyphenyl)-N-[2-(3,4-dimethoxyphenyl) ethyl]-2-azabicyclo[2,2,2]oct-5-yl]-4-nitrobenzamide hydrochloride.

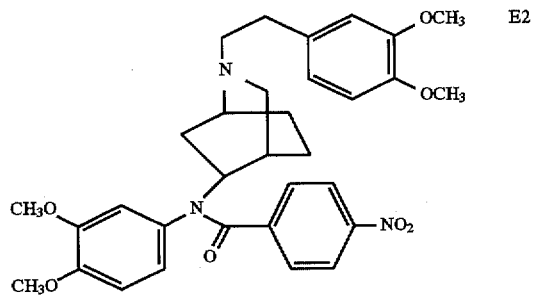

A mixture containing 65 mg (0.15 mmol) of N-(3,4-dimethoxyphenyl)-2-[2-(3,4-dimethoxy-phenyl)ethyl]-2-azabicyclo[2.2.2]octan-5-amine (D5), 24 mg (0.24 mmol) of triethylamine, and 41 mg (0.22 mmol) in 4 ml CH$_2$Cl$_2$ was stirred at room temperature for 1 h. The reaction mixture was then washed with brine, dried over MgSO$_4$, and concentrated in vacuo. Purification by flash chromatography on silica gel (methylene chloride:methanol 95:5 as eluent) afforded clean separated stereoisomers (62 mg all together) as amorphous solids. Each stereoisomer was then submitted to the following procedure: 250 mg of one stereoisomer (0.43 mmol) was dissolved in methylene chloride and dried over MgSO$_4$. After filtration, the solution was concentrated in vacuo. The residue was taken up with methanol and etheral HCl. The solution was concentrated in vacuo and the residue was triturated with diethyl ether and dried in vacuo giving rise to 130 mg of a yellow foam. m.p. around 140° C.

$^1$H NMR (CDCl$_3$)δ(ppm): Stereoisomer I (presence of two protomers) 1.65–2.55(m,5H); 2.60–3.70(m,9H); 3.70–4.00(singlets,12H); 4.55–4.80(m,1H); 6.40–6.85(m, 6H); 7.45(dd,J=8.7Hz,2H); 8.04(dd,J$_1$=3.15Hz,J$_2$=8.75Hz, 2H); 12.00+12.30(two broad s, 1H exchangeable with D$_2$O). Stereoisomer II (presence of two protomers) 1.50–2.30(m, 5H); 2.40–3.55(m,8H); 3.60–4.05(m,13H); 4.75–5.05(m, 1H); 6.35–6.90(m,6H); 7.38(dd,J$_1$=3Hz,J$_2$=8.7Hz,2H); 8.02 (m,2H); 12.4(broad s, 1H exchangeable with D$_2$O).

Pharmacological Data

Methodology

Guinea pigs (300–350 g) were anesthetized by intravenous injection of sodium pentobarbital (60 mg/kg). After thoracotomy the heart was rapidly excised and placed in oxygenated Tyrode solution. Papillary muscles were removed from the right ventricle. Preparations were then fixed to the silastic base of a 5 ml organ bath and superfused with oxygenated Tyrode solution maintained at 37°±1° C.

The modified Tyrode solution (pH 7.35) contained the following (mM): NaCl 125, KCl 4.0, $MgCl_2$ 0.5, $CaCl_2$ 1.8, $NaHCO_3$ 24, $NaH_2PO_4$ 0.9 and glucose 5.5. The solution was equilibrated with a gas mixture of 95% $O_2$–5% $CO_2$.

After a stabilisation period (at least 1 h), transmembrane action potentials were recorded with conventional microelectrodes (10 MOhm) connected to a high input impedance amplifier (BIOLOGIC VF 180). External stimuli were delivered to the preparation with bipolar platinum electrodes placed at one end of the muscle. The pulse duration was 1 ms and the amplitude was twice threshold. The basic cycle length was 1000 ms (PULSAR 6i stimulator). The signals were monitored on a storage oscilloscope (GOULD 1602) and simultaneously recorded on a digital tape recorder (BIOLOGIC DTR 1200) for further analysis.

Measurements were made on resting membrane potential (RMP), action potential amplitude (APA) and action potential durations at 30, 50, and 90% repolarization (APD30, APD50 and APD90 respectively). Recordings were made after 30 min of equilibration for each concentration. Only recordings in which the same impalement was maintained throughout the entire experiment were used for analysis.

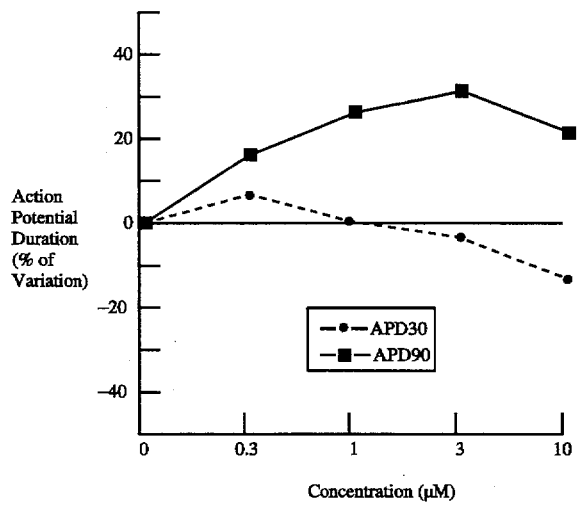

Toxicology: No toxicological effects were indicated for the compounds of the invention in the above mentioned tests.

We claim:

1. A compound of formula (I):

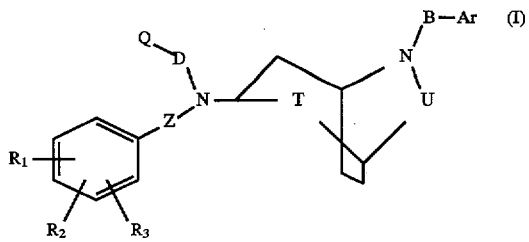

or a salt thereof, or a solvate thereof, wherein

B represents a $C_{1-4}$ n-alkylene group wherein each carbon is optionally substituted by a $C_{1-6}$ alkyl group; .

Z represents a bond, $CH_2$, $(CH_2)_2$ or $X—CH_2—CH_2$ wherein X represents O or S;

D represents CO, $SO_2$, NH—CO or NH—$SO_2$;

T represents a bond and U represents $CH_2$ or T represents $CH_2$ and U represents a bond;

Q represents aryl, aralkyl, aralkenyl or aralkynyl, wherein the aryl moiety may be unsubstituted or substituted with 1 to 5 substituents selected from the list consisting of nitro, halogen, alkylsulfonamido, acylamido, 1H-imidazolyl, alkyl or haloalkyl, or Q represents substituted or unsubstituted: furanyl, pyranyl, thienyl, thiazolyl, imidazolyl, triazolyl or the benzo fused equivalents of furanyl, pyranyl, thienyl, thiazolyl, 1H-imidazolyl or triazolyl, indolyl, oxoindolyl, indenyl, isoindenyl, indazolyl, indolizinyl or pyridinyl or cycloalkyl optionally fused to an aryl group;

$R_1$, $R_2$ and $R_3$ each independently represents H, alkyl, OH or alkoxy or, if attached to adjacent carbon atoms, any two of $R_1$, $R_2$ or $R_3$ together with the carbon atoms to which they are attached may form a fused heterocyclic ring of five or six atoms wherein one, two or three of the said atoms are oxygen or nitrogen;

Ar represents substituted or unsubstituted aryl, wherein the optional substituents are the above defined $R_1$, $R_2$ and $R_3$.

2. A compound according to claim 1, when B represents $CH_2CH_2$.

3. A compound according to claim 1, wherein Z represents a bond.

4. A compound according to claim 1, wherein T represents a bond and U represents $CH_2$.

5. A compound according to claim 1 wherein T represents $CH_2$ and U represents a bond.

6. A compound according to claim 1, wherein D represents CO.

7. A compound according to claim 1, wherein Q is a nitrophenyl group.

8. A compound according to claim 1 being:

N-(3,4-dimethoxyphenyl)-N-[8-[2-(3,4-dimethoxyphenyl)ethyl]-8-aza-bicyclo[3.2.1]oct-3-yl]-4-nitrobenzamide;

N-(3,4-dimethoxyphenyl)-N-[2-(3,4-dimethoxyphenyl)ethyl]-2-azabicyclo[2.2.2]oct-5-yl]-4-nitrobenzamide;

or a salt thereof or a solvate thereof.

9. A pharmaceutical composition comprising a compound of formula (I), as defined in claim 1, or a pharmaceutically acceptable salt thereof and/or a pharmaceutically acceptable solvate thereof, and a pharmaceutically acceptable carrier.

10. A method for the treatment and/or prophylaxis of arrhythmia in a human or non-human mammal which comprises administering an effective, non-toxic, amount of a compound of formula (I) as defined in claim 1, or a pharmaceutically acceptable salt thereof and/or a pharmaceutically acceptable solvate thereof to a human or non-human mammal in need thereof.

* * * * *